United States Patent [19]

Ewing et al.

[11] Patent Number: 6,111,151
[45] Date of Patent: Aug. 29, 2000

[54] REMOVAL OF WATER FROM PROCESS STREAMS

[75] Inventors: Paul Nicholas Ewing, Warrington; Paul David Bernard Bujac, Taporley; David William Bonniface, Warrington, all of United Kingdom

[73] Assignee: Imperial Chemical Industries PLC, London, United Kingdom

[21] Appl. No.: 09/242,053

[22] PCT Filed: Aug. 5, 1997

[86] PCT No.: PCT/GB97/02104

§ 371 Date: Feb. 8, 1999

§ 102(e) Date: Feb. 8, 1999

[87] PCT Pub. No.: WO98/06685

PCT Pub. Date: Feb. 19, 1998

[30] Foreign Application Priority Data

Aug. 10, 1996 [GB] United Kingdom .................... 9616879

[51] Int. Cl.[7] ........................... C07C 17/38; C07C 19/08; C07C 17/08

[52] U.S. Cl. ........................... 570/177; 570/142; 570/165

[58] Field of Search .................................. 570/177, 165, 570/142

[56] References Cited

U.S. PATENT DOCUMENTS 5,334,784  8/1994  Blake et al. ............................. 570/177

FOREIGN PATENT DOCUMENTS 2056977  3/1981  United Kingdom .
93/11853  6/1993  WIPO .

*Primary Examiner*—Alan Siegel
*Attorney, Agent, or Firm*—Cook, Alex, McFarron, Manzo, Cummings & Mehler, Ltd.

[57] ABSTRACT

Process for removing water from compositions containing water, organics and hydrogen fluoride (e.g. product stream from vapour phase hydrofluorination processes, e.g. manufacture of HFA 134*a*, HFA 125 or HFA 32) by phase separation and purge of the aqueous layer.

12 Claims, 3 Drawing Sheets

REMOVAL OF WATER FROM PROCESS STREAMS

This invention relates to a process for the removal of water from process streams and in particular to a process for the removal of water from process steams which are generated during vapour phase catalytic hydrofluorination reactions which employ hydrogen fluoride as the hydrofluorinating reactant.

Recently much attention has been directed at the conception and development of process routes for the production of hydrofluoroalkanes (HF As) which have been proposed as replacements and indeed are now produced and sold as replacements for chlorofluorocarbons.

Amongst the many processes which have been proposed for the production of hydrofluoroalkanes, for example pentafluoroethane (HF A 125), 1,1,1,2-tetrafluoroethane (HFA 134a), difluoromethane (HFA 32) and 1,1,1-trifluoroethane (HFA 143a), vapour phase catalytic hydrofluorination of halogenated, particularly chlorinated alkanes and/or alkenes have received much attention. However a problem with these processes is that during the process, water may be generated as a by-product from reaction of hydrogen fluoride with the catalyst or as a product of catalyst regeneration processes, or indeed, the hydrogen fluoride starting material may contain small amounts of water. If steps are not taken to remove this water, then the concentration of water will increase. Hydrogen fluoride/water mixtures are especially corrosive, and are both difficult and expensive to handle. Moreover water, even at low levels, may act as a catalyst poison.

In the past it has been proposed to remove the water by providing a distillation column which is dedicated to separating substantially anhydrous hydrogen fluoride from a water/hydrogen fluoride mixture. However, such a column must be made of exotic corrosion resistant materials and is expensive.

We have now devised a process by which water may be removed from a process stream and which is cheaper and simpler to operate and eliminates or at least substantially reduces the need for a distillation column which is dedicated to separating substantially anhydrous hydrogen fluoride from water/hydrogen fluoride mixtures.

According to a first aspect of the invention there is provided a process for the removal of water from a process stream which comprises hydrogen fluoride, water, organic products and by-products and unreacted organic starting materials which comprises (i) separating the process stream into a lighter tops stream comprising hydrogen fluoride and lighter boiling organic components from a heavy bottoms stream comprising hydrogen fluoride, water and heavier organic components characterised in that (ii) the heavy bottoms stream is fed to a phase separator under conditions of temperature and pressure such that the heavy stream is in the liquid phase and an organic fraction is separated from a hydrogen fluoride fraction containing water and (iii) disposing of at least a part of the hydrogen fluoride fraction.

We have realised that by performing step (i), which typically comprises separation of a tops vapour from a bottoms liquid, usually by distillation, a degree of separation of hydrogen fluoride from water is achieved there by concentrating up the water in the hydrogen fluoride bottoms phase such that when this bottoms phase undergoes phase separation, the hydrogen fluoride phase contains significantly higher concentration of water than the original process stream, there by allowing the removal of less hydrogen fluoride with the water to be disposed of.

Typically the hydrogen fluoride/water fraction from the phase separator will be divided into a recycle stream, which can be vaporised, to which further hydrogen fluoride is added, and a smaller hydrogen fluoride/water stream which may be further treated or disposed of, for example by being sent to aqueous scrubbers.

The relative proportions of the fraction which is recycled and the fraction which is sent to further treatment will depend particularly upon the rate at which water is produced in the process, but usually the amount of the hydrogen fluoride fraction disposed of will be such as to maintain the concentration of water in the process stream prior to the present invention at less than 0.5%, preferably less than 0.3% and especially less than 0.2% by weight.

The processes from which the composition which is treated according to the present invention is obtained are varied but they will typically be catalytic vapour phase hydrofluorination reactions, and particularly the vapour phase hydrofluornation of a halogenated alkane or alkene, especially a chlorinated alkane or alkene. The process of the invention may be advantageously employed with compositions obtained from the reaction of hydrogen fluoride with a halogenated C1–C4 alkane or alkene in the vapour phase and in the presence of a catalyst.

Particular processes from which a composition may be treated according to the invention include production of HFA 134a, HFA 125, HFA 32, HFA 143a etc. HFA 134a may be produced from 1,1,1 trifluoroethane 2-chloroethane and/ or trichloroethylene. HFA 125 may be produced from perchloroethylene. HFA 32 may be produced from an α-fluroether, for example bis-fluoromethlyether, or from methylene chloride. Conditions of temperature and pressure, preferred fluorination catalysts, proportions of reactants, the arrangement of reactors and methods of recovering pure HFA product have been well documented and are well known in the art, for example as described in EP 0 449 617 and EP 0 449 614 for HFA 134a, in WO94/21579 and WO94/21580 for HFA 32, in WO92/16479 and WO94/ 16482 for HFA 125 and in EP 502 605 for vapour phase fluorinations generally, the contents of all of which are hereby incorporated by reference.

For clarity, the invention will now be described with reference to a composition which has been produced by the vapour phase fluorination of perchloroethylene to produce pentafluoroethane, although the invention is not so limited.

A further aspect of the invention provides a process for the production of hydrofluorocarbon which comprises contacting a precursor compound with hydrogen fluoride in the vapour phase in the presence of a hydrofluorination catalyst to produce a product stream comprising the hydrofluorocarbon, organic by-products, hydrogen fluoride and water and treating at least part and preferably substantially all of the product stream, optionally after prior treatment, in a process according to the first aspect of the invention.

As desired, more than one hydrofluorocarbon may be produced in the process by co-production with another hydrofluorocarbon. Suitably the precursor compound for one or more hydrofluorocarbon products may be fed into the phase separator or if present the recycle stream as desired for subsequent fluorination to the hydrofluorocarbon product. By way of example, HFC 125 and HFC 134a may be co-produced by feeding perchioroethylene and trichloroethylene into the phase separator and HFC 125 and HFC 32 may be co-produced by feeding perchloroethylene and methylene chloride into the separator.

The amount of water produced during these processes and thus the concentration of water in the process off-gas depends in particular upon the particular catalyst employed since certain catalysts have a tendency to produce more by-product water than others. Thus, fluorination catalysts which comprise a high proportion of metallic oxides will have a tendency to produce more water than fluorination catalysts which contain a smaller proportion of metallic oxides and more metallic halides. Although all catalysts have a tendency to by-produce water during hydrofluorination processes and more particularly during regeneration thereof, catalysts which are based upon metal oxides, or mixed metal oxides, for example chromia, alumina and other metallic oxides supported on chromia or alumina, for example zinc, iron, magnesium, nickel tend to produce levels of water which make it essential to provide a highly efficient water removal process step.

In the hydrofluorination of perchloroethylene, we particularly prefer to employ a catalyst as described in EP 0 502 605, the contents of which are incorporated herein by reference.

The off-gas composition from the process typically comprises a major proportion of hydrogen fluoride and hydrogen chloride, pentafluoroethane, chlorotetrafluoroethane and dichlorotrifluoroethane together with minor quantities of various chlorofluoroethane by-product impurities, unreacted perchloroethylene and by-product water.

Prior to the process according to the invention, the stream needs to be liquefied, and this may be achieved for example by distillation by partial condensation, or by the use of a "quench" which is essentially a single or multiple stage column to which no heat other than that of the reactor off-gas fed to it, is input. During the liquefaction step, the volatile components of the stream are removed from the top of a column as a vapour and may then be sent to further purification stages to recover pentafluoroethane. A cooled liquid is recovered from the bottom of the column which comprises unreacted perchloroethylene, hydrogen fluoride, water, dichlorotrifluoroethane, trichlorodifluoroethane and minor amounts of unsaturated impurities. This liquid is then fed to the process of the invention, and preferably a vessel in which the liquid is allowed to reside for a time sufficient to allow satisfactory phase separation of the liquid into a lower organic fraction which may be recycled to the process, and an upper fraction containing mainly hydrogen fluoride in which the water has effectively been significantly concentrated.

The conditions under which the process is effected are not critical provided that the conditions are such that the stream to be phase separated is in the liquid phase. It is convenient however to effect the process of the invention at about atmospheric pressure or superatmospheric pressures up to about 20 barg and preferably up to about 10 barg and at ambient temperature, although temperatures in the range from −80° C. to 40° C. or higher may be employed if desired, and subatmospheric or superatmospheric pressures may also be employed.

The top hydrogen fluoride fraction containing water may then be divided into a stream for further treatment and a stream which may be recycled to the process. The proportion of the top fraction which is sent for further treatment versus recycle depends upon the amount of water produced, the efficiency of the phase separation and the concentration of water which can be tolerated during the hydrofluorination process.

Generally, we prefer that the proportion which is recycled to the process contains a concentration of water relative only to the hydrogen fluoride present of less than 0.5%, preferable less than 0.3% and especially less than 0.2%, and thus sufficient of the tops fraction is sent to further treatment such that after the addition of further hydrogen fluoride to the hydrogen fluoride/water which is recycled, the concentration of water relative to hydrogen fluoride is within these limits. As a guide only, this will usually require that between 2% and 5% of the tops fraction is disposed of. This may be achieved simply by pumping the tops fraction out of the vessel or allowing the tops fraction to drain from the vessel.

The invention is illustrated with reference to the following figures in which.

Figure 1:
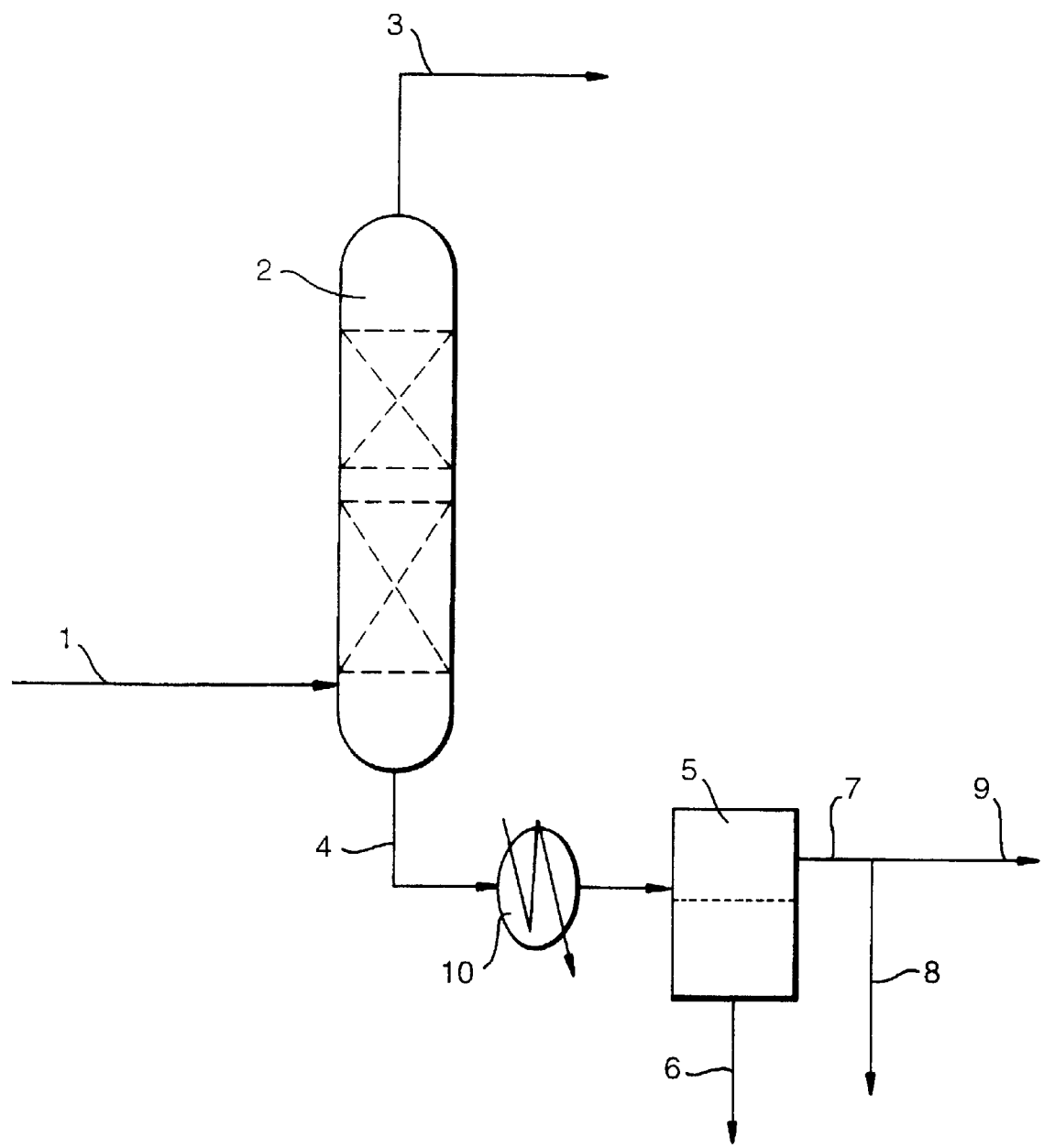
FIG. 1 is a schematic flow-sheet of the process of the invention.

In FIG. 1, a typical reactor off-gas stream (1) from the vapour phase hydrofluorination of perchloroethylene to produce pentafluoroethane over a zinc on chromia catalyst and containing 23 kg/hr HF, 16 kg/hr HCl, 12 kg/hr HFA 125, 21 kg/hr HCFC 124, 15 kg/hr HCFC 123, 10 kg/hr perchloroethylene and other minor components including HCFC 122, HCFC 1112 and 0.1 kg/hr of water is fed to a distillation column (2) in which a lights stream (3) containing 16 kg/hr HCl, 12 kg/hr 125, 18 kg/hr124, 1 kg/hr 123 and 2 kg/hr HF is separated from a heavies stream (4) containing 14 kg/hr 123, 10 kg/hr Per, 21 kg/hr HF, and 0.1 kg/hr water. The latter stream is fed via a cooler (10) to a phase separation vessel (5) in which an organics rich phase (6) is separated from an HF rich phase containing over 90% of the water (7). An HF/water purge stream (8) is taken from stream (7) for further treatment, while the stream (9), containing at least 90% by weight of stream (7) is recycled to the fluorination reactors.

Figure 2:
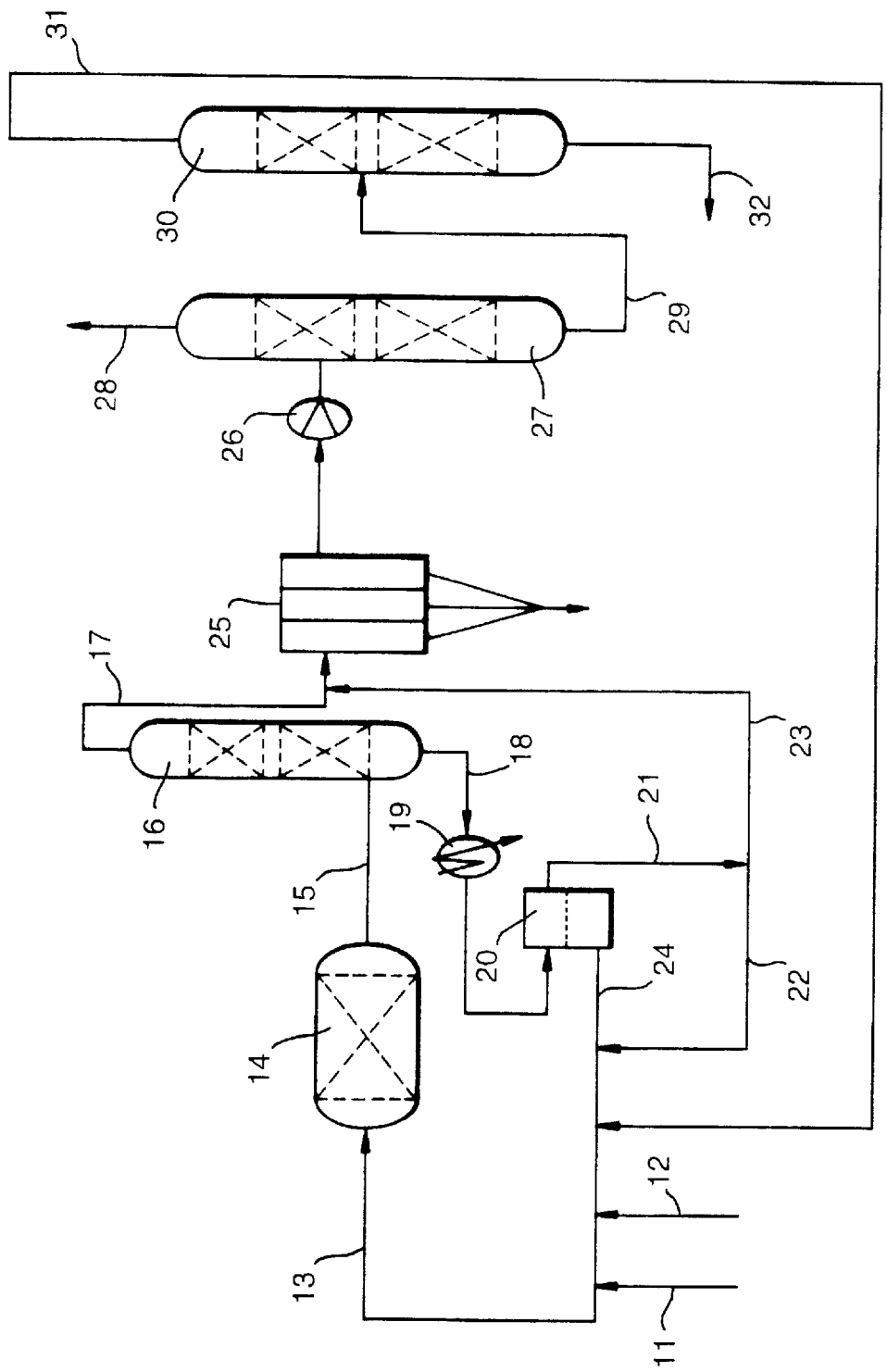
FIG. 2 is a schematic flow-sheet for the production of pentafluoroethane from perchloethylene including the steps of distillation and phase separation.

In FIG. 2, a fluorination reactor (14) is fed a stream (13) comprising Per (11) and HF (12) feeds and recycle streams (24), (22) and (31). The off-gas from the reactor, (15), is fed to a distillation column (16) in which a lights stream (17) comprising mainly HCl, 125, 124 and HF, with minor amounts of 114a and 133a, is separated from a heavies stream (18) comprising HF, 123,122, Per, 1112, and other underfluorinated intermediates to 125. This latter stream is fed to a cooler (19) before entering a phase separation vessel (20) in which an HF rich stream (21) is separated from an organics rich stream (24). The water content of stream (18) is concentrated up in stream (21). Stream (22), containing the majority of stream (21), is recycled to the reactors. Stream (23), containing a small proportion of stream (21) is disposed of in aqueous scrubbing system (25).

The lights stream (17) is fed to an aqueous scrubbing and drying stage (25), in which HCl and HF is stripped from the organics. The acid free organics are fed to compressor (26), prior to distillation in column (27) in which a 125 stream (28) is separated from the 124 containing stream (29). This stream is fed to a final distillation column, (30) in which a 124 recycle stream (31) is separated from stream (32) containing 114a and 133a. The latter stream is removed from the process for further treatment.

Figure 3:
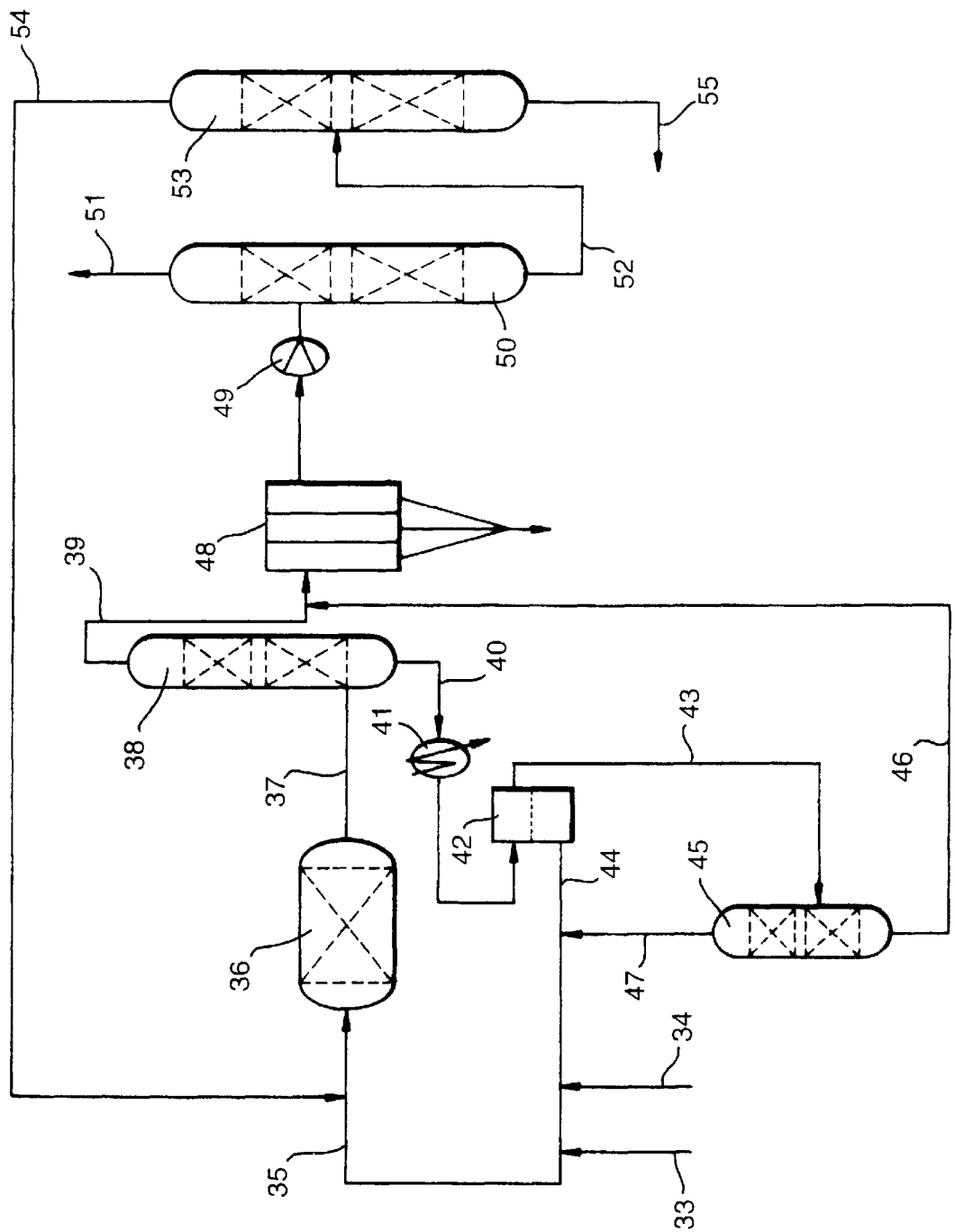
FIG. 3 is a schematic flow-sheet for the production of pentafluoroethane from perchloroethylene including the steps of distillation and phase separation and in which an additional water/hydrogen fluoride distillation step is also shown.

In FIG. 3, a fluorination reactor (36) is fed a stream (35) comprising Per (33) and HF (34) feeds and recycle streams (44), (47) and (54). The off-gas from the reactor, (37), is fed to a distillation column (38) in which a lights stream (39)

comprising mainly HCl, 125, 124 and HF, with minor amounts of 114a and 133a, is separated from a heavies stream (40) comprising HF, 123,122, Per, 1112, and other underfluorinated intermediates to 125. This latter stream is fed to a cooler (41) before entering a phase separation vessel (42) in which an HF rich stream (43) is separated from an organics rich stream (44). Stream (43) is fed to 10 distillation column (45) in which an HF recycle stream (47) is separated from a stream containing HF and water (46). The latter stream can be fed to aqueous scrubbing system (48) in which the acid content is diluted prior to neutralisation.

The lights stream (39) is fed to an aqueous scrubbing and H2SO4 drying stage (48), in which HCl and HF is stripped from the organics. The acid free organics are fed to compressor (49), prior to distillation in column (50) in which a 125 stream (51) is separated from the 124 containing stream (52). This stream is fed to a final distillation column, (53) in which a 124 recycle stream (54) is separated from stream (55) containing 114a and 133a. The latter stream is removed from the process for further treatment.

The advantage of this FIG. 3 scheme over the FIG. 2 scheme is that the HF losses are minimised by further distillation of the HF/H20 stream to give anhydrous HF and [as a limit] HF/H20 azeotrope; however the additional capital cost of the HF still has to be offset against this improvement in HF efficiency.

The invention is further illustrated but not limited by the following examples.

EXAMPLE 1

Hydrogen fluoride, perchioroethylene and water were mixed in the quantity by weight given in Table 1 below and were charged to a 300 ml FEP (copolymer of tetrafluoroethylene and hexafluoropropylene) separating vessel, mixed well and allowed to phase separate for about 10 minutes. Samples of the lower perchloroethylene(per) rich phase and lower hydrogen fluoride rich phase were taken and analysed for their water content by Karl-Fisher titration.

The phase separation vessel was attached to a scrubbing train to allow discharge of the denser per rich phase into a series of ice and water scrubbers. The separation vessel was reweighed after discharge of the perchloroethylene phase to give the weight of the perchloroethylene phase (by difference) and the acid content of this perchloroethylene rich phase was obtained by titration of the combined ice and water scrubber liquors.

Five runs were conducted following the above procedure but for each run a different compositional mixture of perchloroethylene, hydrogen fluoride and water (as detailed in Table 1 below) was employed, all runs being conducted at 22° C. and atmospheric pressure.

The experimental results are summarised in the Table 1 below.

As indicated in the Table below, $H_2O$ is concentrated in the HF rich phase, rather than the perchloroethylene rich phase.

TABLE 1

| Wt HF (g) | Wt Per (g) | Wt $H_2O$ (g) | Wt of per rich phase | Wt of HF in per rich phase | $H_2O$ in per rich Phase (g) | $H_2O$ in HF rich phase (g) |
|---|---|---|---|---|---|---|
| 90 | 8.1 | 5 | 8 | 0.16 | 0.1 | 4.9 |
| 90 | 8.1 | 5 | 8 | 0.17 | 0.09 | 4.91 |
| 90 | 48.6 | 5 | 49 | 1 | 0.22 | 4.78 |
| 90 | 48.6 | 5 | 49 | 1.1 | 0.17 | 4.83 |
| 90 | 97.2 | 5 | 99 | 1.9 | 0.26 | 4.74 |

EXAMPLE 2

Hydrogen fluoride perchloroethylene, HCFC 123 and water were mixed, in the quantity by weight shown in Table 2 below, and were charged to a stainless steel vessel. The vessel was shaken vigorously to ensure good mixing and then allowed to stand for about 10 minutes while phase separation took place.

Samples of the lower organic phase were taken and analysed for water and HF content. The remainder of the organic phase was then discharged and the vessel was then reweighed. This enabled the weights of both the organic and inorganic phases to be calculated. Samples of the inorganic phase were then taken and analysed for water content.

Two runs were conducted following this procedure, the ratio of perchloroethylene to HCFC 123 being varied in each run. Both runs were conducted at room temperature and around atmospheric pressure. The results are summarised in Table 2 below.

These results show clearly that most of the water charged to the system is concentrated into the HF-rich phase.

TABLE 2

| Wt HF (g) | Wt Per (g) | Wt HCFC 123 (g) | Wt of $H_2O$ (g) | Wt of HF in per rich phase | $H_2O$ in per rich Phase (g) | $H_2O$ in HF rich phase (g) |
|---|---|---|---|---|---|---|
| 48.5 | 36.4 | 12.1 | 0.4 | 0.08 | 0.08 | 0.32 |
| 48.5 | 12.2 | 36.6 | 0.36 | 0.04 | 0.08 | 0.28 |

What is claimed is:

1. A process for the removal of water from a process stream which includes hydrogen fluoride, water, organic hydrofluorocarbon products and by-products and unreacted organic starting materials which comprises (i) separating a lighter tops stream comprising hydrogen fluoride and lighter boiling organic components from a heavy bottoms stream comprising hydrogen fluoride, water and heavier organic components characterized in that (ii) the heavy stream is fed to a phase separator under conditions of temperature and pressure such that the heavy stream is in the liquid phase and separating an organic fraction from a hydrogen fluoride fraction containing water and (iii) disposing of at least a part of the hydrogen fluoride fraction outside of the process.

2. A process according to claim 1 which comprises separating the hydrogen fluoride fraction containing water into a recycle stream and a further hydrogen fluoride stream containing water.

3. A process according to claim 2 in which further hydrogen fluoride is added to the recycle stream.

4. A process according to claim 2 in which the relative proportions of the fraction which is separated as the further hydrogen fluoride stream and as the recycle stream are such that the concentration of water in the process stream prior to separation into the lighter tops and heavy bottoms stream is maintained at a level of less than 0.5% by weight.

5. A process according claim 1 in which the process stream is obtained by the catalytic vapour phase hydrofluorination of a halogenated alkane or halogenated alkene.

6. A process for the production of a hydrofluorocarbon which comprises contacting a precursor compound with hydrogen fluoride in the vapour phase in the presence of a hydrofluorination catalyst to produce a product stream comprising the hydro-fluorocarbon, organic by-products, hydrogen fluoride and water and treating at least part of the product stream, in a process according to claim 1.

7. A process according to claim 6 in which substantially all of the product stream is treated.

8. A process according to claim 6 in which the hydrofluorocarbon comprises 1,1,1,2 tetrafluoroethane and the precursor comprises 1,1,1-trifluoro-2-chloroethane and/or trichloroethylene.

9. A process according to claim 6 in which the hydrofluorocarbon comprises pentafluoroethane and the precursor comprises perchloroethylene.

10. A process according to claim 6 in which the hydrofluorocarbon comprises difluoromethane and the precursor comprises an α-fluoroether.

11. A process according to claim 10 in which the ether comprises bis-fluoromethylether.

12. A process according to claim 10 in which the precursor comprises methylene chloride.

* * * * *